United States Patent [19]
Datta et al.

[11] Patent Number: 5,611,986
[45] Date of Patent: Mar. 18, 1997

[54] MEDICAL DEVICES CONTAINING HIGH INHERENT VISCOSITY POLY(P-DIOXANONE)

[75] Inventors: Arindam Datta, Hillsborough, N.J.; Rohit Tandon, Flowery Branch, Ga.; I-Jen Chen, Princeton; Bethany A. Canterberry, Stockton, both of N.J.; Scott E. Fitzgerald, Nazareth, Pa.

[73] Assignee: Ethicon, Inc., Somerville, N.J.

[21] Appl. No.: 270,712

[22] Filed: Jul. 5, 1994

[51] Int. Cl.⁶ .................. B29F 1/06; B29F 1/08
[52] U.S. Cl. .............. 264/328.16; 264/234; 264/328.1; 264/331.11; 528/348; 528/354
[58] Field of Search .................. 528/348, 354; 525/411, 415; 128/335.5, 325, 334 R; 264/328.16, 331.11, 234, 328.1

[56] References Cited

U.S. PATENT DOCUMENTS

| | | | |
|---|---|---|---|
| 3,063,967 | 11/1962 | Schultz | 260/78.3 |
| 3,063,968 | 11/1962 | Schultz | 260/78.3 |
| 4,052,988 | 6/1977 | Doddi et al. | 128/335 |
| 4,326,522 | 4/1982 | Guerrero et al. | 128/260 |
| 4,490,326 | 12/1984 | Beroff et al. | 264/328 |
| 4,591,630 | 5/1986 | Gertzman | 528/503 |
| 4,620,541 | 11/1986 | Gertzman et al. | 128/326 |
| 4,643,191 | 2/1987 | Bezwada et al. | 128/335.5 |
| 4,646,741 | 3/1987 | Smith | 128/334 |
| 4,653,497 | 3/1987 | Bezwada et al. | 128/335.5 |
| 4,889,119 | 12/1989 | Jamiolkowski et al. | 606/220 |
| 4,890,613 | 1/1990 | Golden et al. | 606/220 |
| 4,955,913 | 9/1990 | Robinson | 606/228 |
| 5,007,923 | 4/1991 | Bezwada et al. | 606/231 |
| 5,013,315 | 5/1991 | Barrows | 606/71 |
| 5,080,665 | 1/1992 | Jarrett et al. | 606/219 |
| 5,160,339 | 11/1992 | Chen et al. | 606/158 |
| 5,201,738 | 4/1993 | Scott et al. | 606/77 |

FOREIGN PATENT DOCUMENTS

| | | |
|---|---|---|
| 0274898A2 | 7/1988 | European Pat. Off. |
| 0415783A2 | 3/1991 | European Pat. Off. |
| 0520177A1 | 12/1992 | European Pat. Off. |

*Primary Examiner*—James J. Seidleck
*Assistant Examiner*—Duc Truong
*Attorney, Agent, or Firm*—Hal Brent Woodrow

[57] ABSTRACT

The present invention discloses polymers of poly(p-dioxanone) having an inherent viscosity in the range of from 2.3 dL/g to about 8 dL/g, as determined at a concentration of 0.1 g/dL in hexafluoroisopropanol at 25° C. This invention also describes improved surgical devices and filaments made from poly(p-dioxanone) with an inherent viscosity in the range of from 2.3 dL/g to about 8 dL/g, determined at a concentration of 0.1 g/dL in hexafluoroisopropanol at 25° C. Additionally, disclosed are processes for manufacturing poly(p-dioxanone) with an inherent viscosity in the range of from 2.3 dL/g to about 8 dL/g, as determined at a concentration of 0.1 g/dL in hexafluoroisopropanol at 25° C., as well as, processes for molding surgical articles and extruding surgical filaments from these polymers.

9 Claims, 6 Drawing Sheets

MEDICAL DEVICES CONTAINING HIGH INHERENT VISCOSITY POLY(P-DIOXANONE)

FIELD OF THE INVENTION

This invention relates to high inherent viscosity polymers of p-dioxanone. More specifically this invention relates to high inherent viscosity polymers of p-dioxanone which are suitable for melt processing into surgical devices and filaments that have improved mechanical properties and in vivo survival rates.

DESCRIPTION OF THE PRIOR ART

Polymers of p-dioxanone were first reported by Schultz et al. in U.S. Pat. No. 3,063,967 and 3,063,968. Schultz describes making poly(p-dioxanone) with intrinsic viscosities of from 1.98 to 2.83 dL/g, determined at 25° C. using a Ubbelohde viscometer at a concentration of 0.5 g per 100 cc of tetrachloroethane using zinc, mercury and cadmium based catalysts. Originally Schultz proposed using these polymers for coatings and textile fibers. However, poly(p-dioxanone) is not suitable for use as a general textile fiber or coating because the polymer is highly susceptible to hydrolysis.

Doddi et al. was the first to recognize that the susceptibility of poly(p-dioxanone) to hydrolysis provided a unique utility for poly(p-dioxanone). In U.S. Pat. No. 4,052,988 Doddi described the use of poly(p-dioxanone) in bioabsorbable medical devices such as surgical sutures, pins, screws and reinforcing plates. Subsequently, medical devices and a process for molding medical devices such as staples and clips from poly(p-dioxanone) were described in U.S. Pat. Nos. 4,490,326 and 4,620,541. The poly(p-dioxanone) polymer used in these inventions generally had an inherent viscosity in the range of from about 1.2 dL/g to about 2.26 dL/g.

Commercially available sutures and suture clips manufactured from poly(p-dioxanone) are made from polymers that have an inherent viscosity in the range of from about 1.6 to about 1.92 dL/g. Polymer with inherent viscosities within this range were convenient to extrude and mold into medical devices because the melt viscosity of these polymers were low enough for conventional extrusion and injection molding. Polymers with higher inherent viscosities were not used because the polymers were very difficult to manufacture and process. Additionally, there was no reason to believe that the incremental improvement in polymer properties would be sufficient to warrant going to higher inherent viscosity polymers. For example, in molding, since the zero shear melt viscosity of poly(p-dioxanone) polymers increases by approximately the fifth power of the inherent viscosity, high inherent viscosity polymers often require working at higher pressures with more expensive molding machinery.

The only other method for making a poly(p-dioxanone) medical device with an inherent viscosity of greater than 2.26 dL/g is disclosed by Hinsch et al. in EPA 274 898. Hinsch describes a method for producing an open cell foam by first polymerizing p-dioxanone at a temperature of from about 120° to 150° C. then adding solvents to the polymer, freeze drying the resulting mixture to form the foam and remove excess unreacted monomer. However, the process for making poly(p-dioxanone) described in Hinsch produces an open cell porous foam material which is unsuitable for melt processing into filaments or medical devices.

As discussed above, the prior art processes for manufacturing poly(p-dioxanone) generally produce polymeric material that has an inherent viscosity under 2.26 dL/g or that is unsuitable for surgical devices. The process described by Schultz uses catalysts that are not approved for medical grades of poly(p-dioxanone), therefore, Schultz's process is not suitable for use in surgical devices. The process disclosed by Doddi produces a poly(p-dioxanone) which is suitable for making surgical devices; however, Doddi did not describe making polymers with an inherent viscosity above 2.26 dL/g. The process disclosed by Hinsch although providing a high molecular weight poly(p-dioxanone) polymer does not produce a material which may be readily incorporated into melt processed surgical devices because of the air entrained in the open cell foam. Additionally, making a poly(p-dioxanone) polymer with an inherent viscosity above 2.26 dL/g is very difficult. The monomer must have a high and consistent purity, and the initiator added to begin polymerization must be precisely determined to assure obtaining the desired molecular weight of poly(p-dioxanone). Therefore, an alternate process needs to be employed to manufacture high inherent viscosity poly(p-dioxanone).

Surprisingly, we have discovered a high inherent viscosity poly(p-dioxanone) that can be melt processed into medical device such as suture clips, sutures and plates, that have significantly improved properties such as longer in vivo survival surgical articles, as well as, greater strength and toughness.

SUMMARY OF THE INVENTION

The present invention provides a polymer of poly(p-dioxanone) suitable for use in surgical devices and surgical filaments having an inherent viscosity of from 2.3 dL/g to about 8 dL/g tested at 25° C. at a concentration of 0.1 g/dL in hexafluoroisopropanol with a bulk density of from about 1.3 g/cc to about 1.45 g/cc and a monomer content of less than 5 percent by weight.

In an additional embodiment of the present invention there is provided a medical device comprising a melt processed device of poly(p-dioxanone) wherein the inherent viscosity of the poly(p-dioxanone) is in the range of from 2.3 dL/g to about 8 dL/g, tested at 25° C. at a concentration of 0.1 g/dL in hexafluoroisopropanol and a bulk density of from about 1.3 g/cc to about 1.45 g/cc.

In another embodiment of the present invention there is provided an improved surgical filament comprising a filament of poly(p-dioxanone) having an inherent viscosity in the range of from 2.3 dL/g to about 3.5 dL/g tested at 25° C. at a concentration of 0.1 g/dL in hexafluoroisopropanol.

In a further embodiment of the present invention there is provided a deformable surgical article comprising a surgical article containing poly(p-dioxanone) having an inherent viscosity in the range of from about 2.10 dL/g to about 3.5 dL/g tested at 25° C. at a concentration of 0.1 g/dL in hexafluoroisopropanol.

In yet another embodiment of the present invention there is provided a process for making a high inherent viscosity poly(p-dioxanone) polymer comprising determining the amount of water, free acid and reactive impurities in a lot of monomer containing at least 80 mole percent p-dioxanone, the balance of the monomer being a lactone monomer selected from the group consisting of glycolide, lactide, ε-caprolactone and trimethylene carbonate; polymerizing the lot of monomers in a suitable reaction vessel under suitable conditions for polymerizing the monomer in the presence of an organo-tin catalyst with a polymerization initiator provided in an amount sufficient after taking into account the presence of the water, free acid and reactive impurities in the lot of monomer to provide a poly(p-dioxanone) containing polymer with an inherent viscosity of greater than 2.3 dL/g.

In yet a further embodiment of the present invention there is provided a process for manufacturing a surgical filament comprising extruding a filament containing poly(p-dioxanone) with an inherent viscosity in the range of from 2.3 dL/g to about 3.5 dL/g at a temperature of in the range of from about 135° C. to about 165° C. to form a filament; then quenching said filament; then drawing said filament to form an oriented filament.

In yet an additional embodiment of the present invention there is provided a process for producing molded surgical devices from high inherent viscosity poly(p-dioxanone) comprising heating poly(p-dioxanone) with an inherent viscosity in the range of from 2.1 dL/g to about 3.5 dL/g to a temperature in the range of from about 105° C. to about 140° C. to melt the poly(p-dioxanone); then injecting said melted poly(p-dioxanone) at a volumetric flow of greater than 0.7 cubic inches per second into a mold being maintained at a temperature above 35° C.; cooling said melted poly(p-dioxanone) sufficiently to maintain its shape while in the mold; and removing said hardened poly(p-dioxanone) from the mold.

DETAILED DESCRIPTION OF THE INVENTION

The use of poly(p-dioxanone) with a high molecular weight or high inherent viscosity results in increased strength for surgical filaments, increased toughness, and a prolonged in vivo survival for articles made from poly(p-dioxanone). For the purpose of this invention a high inherent viscosity (HIV) poly(p-dioxanone) has an inherent viscosity of about 2.10 dL/g or greater. To obtain a medical device with an inherent viscosity of about 2.10 dL/g or greater the initial resin's inherent viscosity prior to melt processing must be higher than 2.10 dL/g. Commonly during melt processing the polymer's inherent viscosity will drop due to polymer degradation that occurs during melt processing. Therefore, the initial inherent viscosity of poly(p-dioxanone) should be in the range of from 2.30 dL/g to about 8 dL/g, preferably in the range of from 2.4 dL/g to about 8 dL/g, more preferably in the range of from 3.25 dL/g to about 8 dL/g and optionally may be in the range of from about 4.6 dL/g to about 8 dL/g tested at 25° C. at a concentration of 0.1 g/dL in hexafluoroisopropanol. Currently, it is preferred that the inherent viscosity of poly(p-dioxanone) as determined from the medical device be in the range of from 2.10 dL/g to about 8 dL/g, preferably in the range of from 2.3 dL/g to about 8 dL/g, more preferably in the range of from 2.4 dL/g to about 8 dL/g, even more preferably in the range of from about 3.25 dL/g to about 8 dL/g and optionally may be in the range of from about 4.6 dL/g to about 8 dL/g tested at 25° C. at a concentration of 0.1 g/dL in hexafluoroisopropanol. For surgical filaments it is specifically preferred that the inherent viscosity of the poly(p-dioxanone) as determined from the filament be in the range of from about 2.3 dL/g to about 3.5 dL/g and preferably in the range of from 2.4 dL/g to 3.5 dL/g. Hereafter, unless otherwise stated all viscosities were determined at 25° C. at a concentration of 0.1 g/dL in hexafluoroisopropanol.

For the purpose of this invention, high inherent viscosity poly(p-dioxanone) polymer shall also include copolymers of poly(p-dioxanone) which contain up to 20 mole percent of another lactone monomer (such as lactide, glycolide, ε-caprolactone or trimethylene carbonate). Although, currently the preferred polymer is poly(p-dioxanone) homopolymer.

Figure 1:
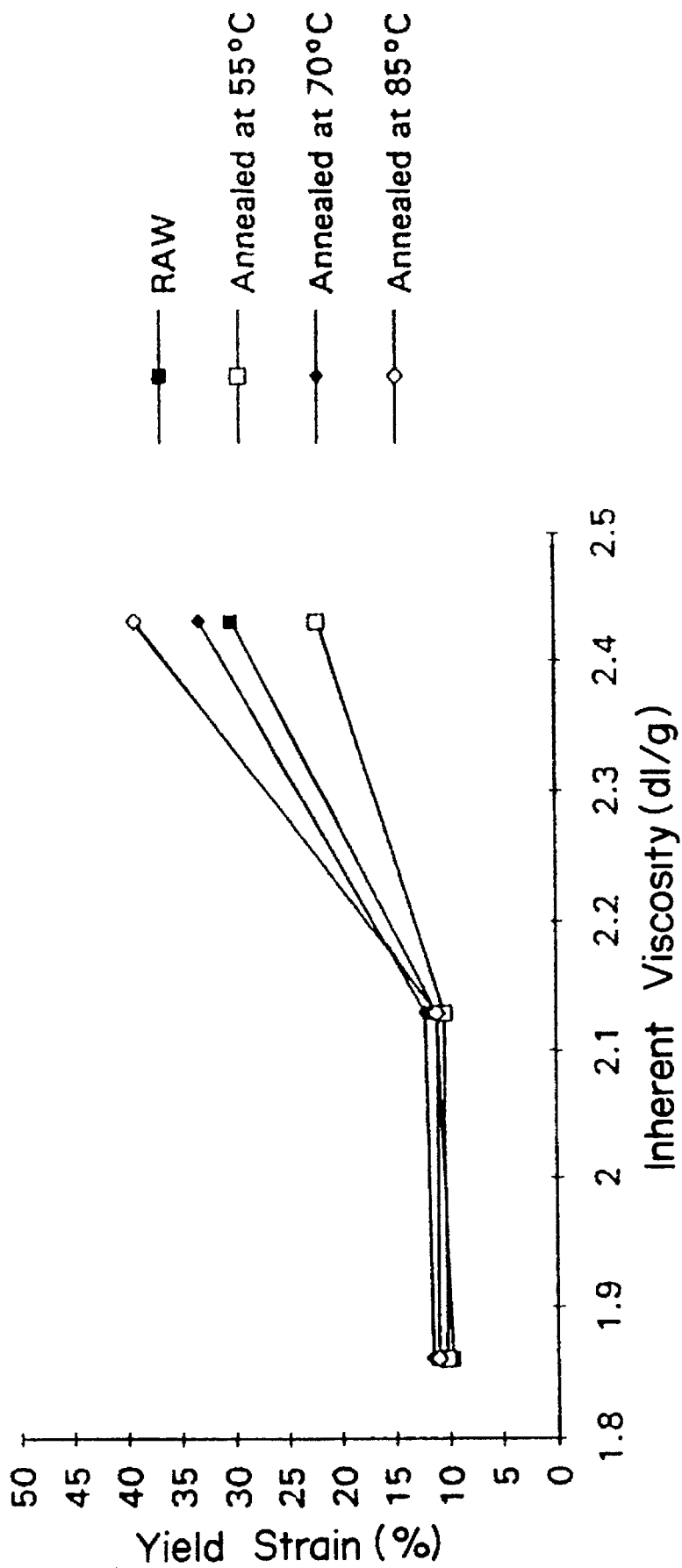
FIG. 1 graphically illustrates the yield strain values obtained from four poly(p-dioxanone) test articles versus the inherent viscosities of the polymers from which the test articles were molded. Three of the four test articles were annealed under an inert atmosphere for eight (8) hours at the indicated temperatures. The fourth test article was not annealed (raw).
Figure 2:
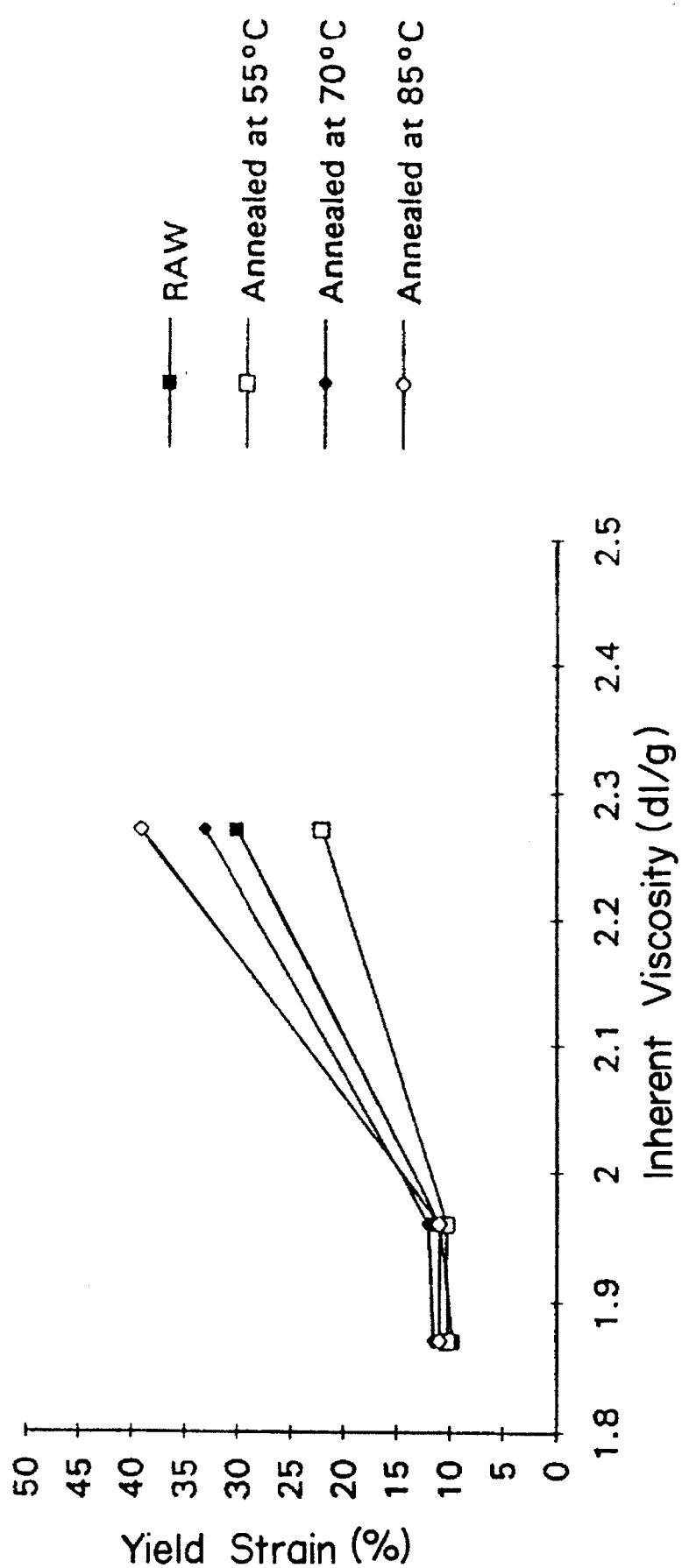
FIG. 2 graphically illustrates the yield strain obtained from four poly(p-dioxanone) test articles versus the inherent viscosity of the polymers contained in the test articles after they were molded. Three of the four test articles were annealed under an inert atmosphere for eight (8) hours at the indicated temperatures. The fourth test article was not annealed (raw).

As shown in FIG. 1 there are significant changes in the properties of poly(p-dioxanone) with increasing inherent viscosity (molecular weight). The graph of yield strain versus inherent viscosity shows that high inherent viscosity poly(p-dioxanone) undergoes permanent deformation at much higher elongation values than articles molded from poly(p-dioxanone) with an initial inherent viscosity of less than about 2.1 dL/g, determined at 25° C. at a concentration of 0.1 g/dL in hexafluoroisopropanol. Molded articles of poly(p-dioxanone) with inherent viscosities of about 2.1 dL/g, determined after molding, also have significantly improved yield strain values. Thus, medical devices made with high inherent viscosity poly(p-dioxanone) will undergo significantly more reversible deformation; that is they will stretch or elongate more before becoming permanently deformed. It is particularly desirable in fashioning hinged surgical clips to have a high yield strain, thereby allowing a single size clip to deform and accommodate a greater range of diameters of surgical sutures. Thus, a surgeon instead of having to select the specific clip for each size suture would be able to use one clip for many sizes of suture. Additionally, having one size of suture clip that will accommodate several sizes of sutures would both reduce hospital and factory costs associated with manufacturing and maintaining clip inventories.

Figure 3:
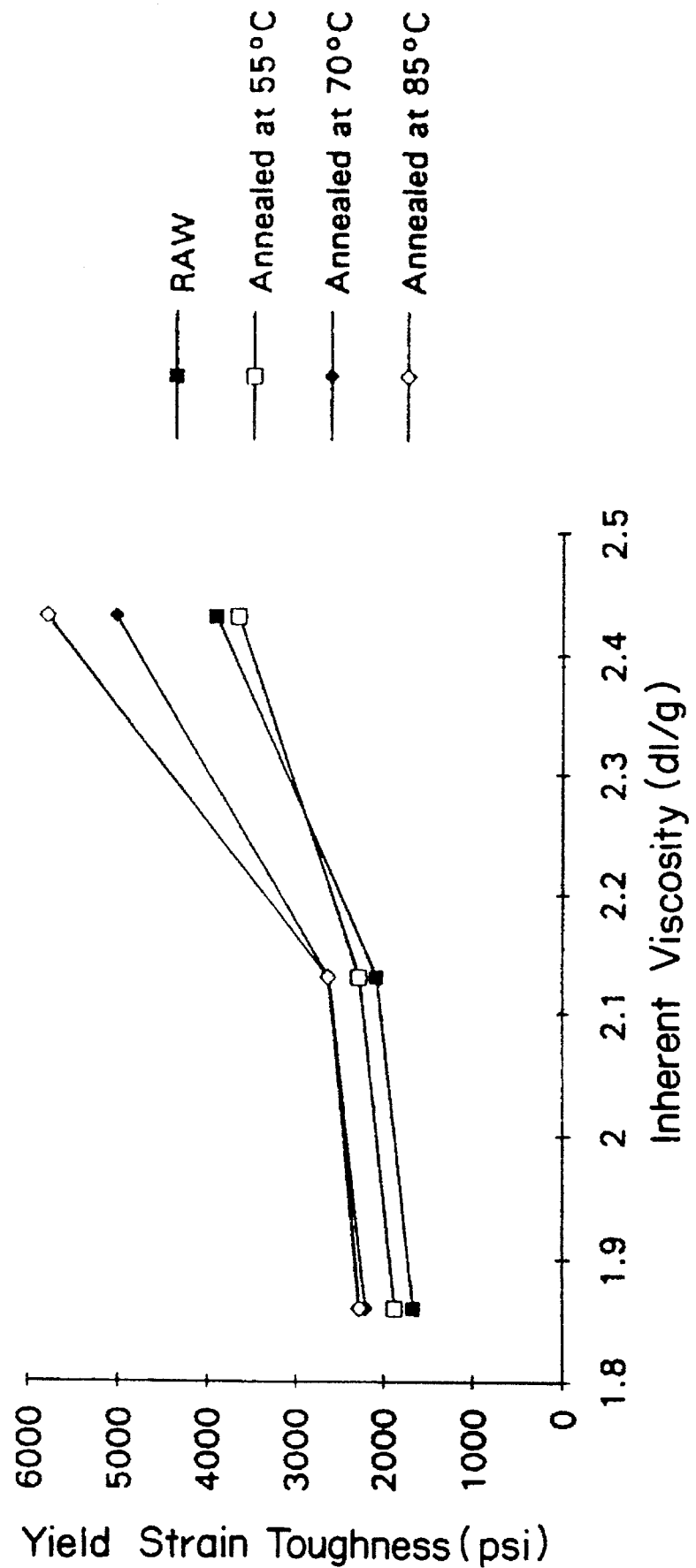
FIG. 3 graphically illustrates the yield strain toughness obtained from four poly(p-dioxanone) test articles versus the inherent viscosity of the polymers from which the test articles were molded. The yield strain toughness was calculated by multiplying the shear stress by the square root of the shear strain. Three of the four test articles were annealed under an inert atmosphere for eight (8) hours at the temperatures indicated. The fourth test article was not annealed (raw).
Figure 4:
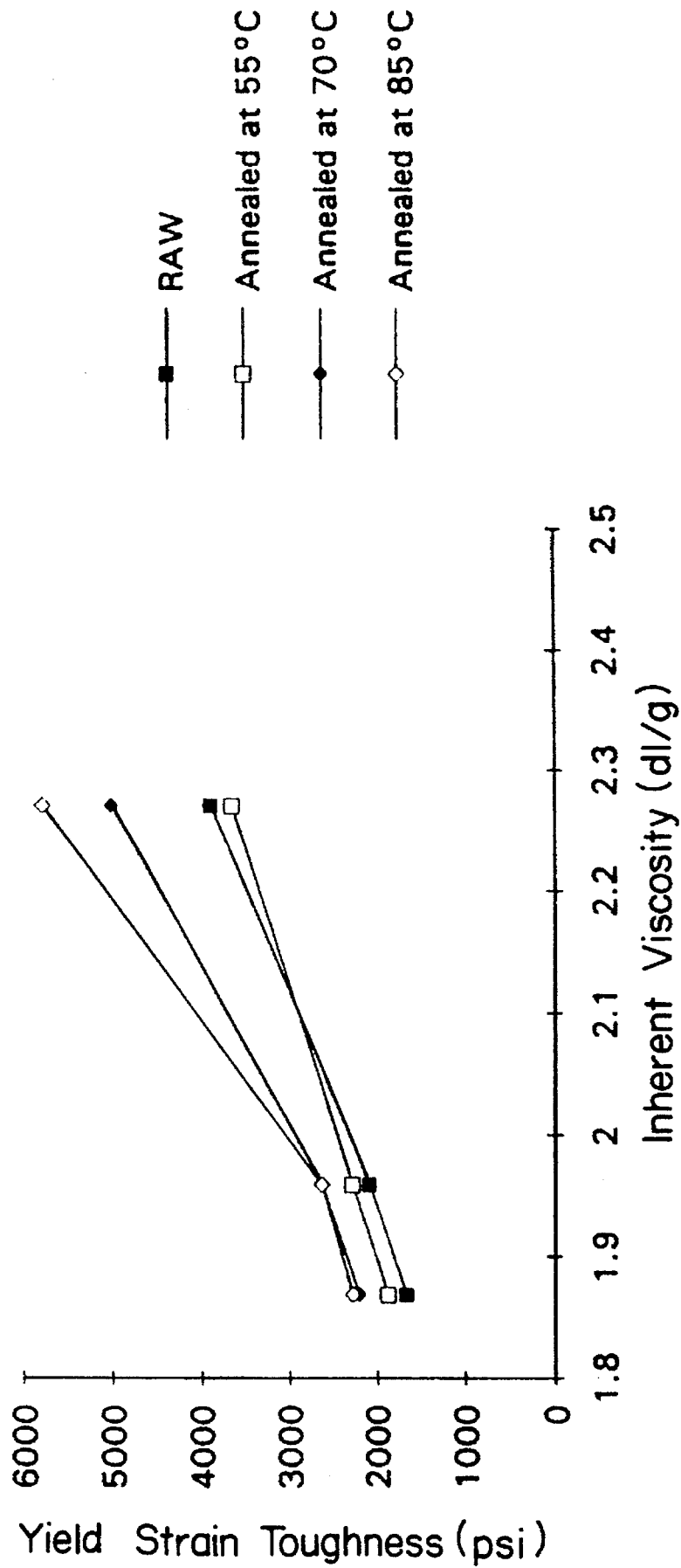
FIG. 4 graphically illustrates the yield strain toughness obtained from four poly(p-dioxanone) test articles versus the inherent viscosities of the polymers contained in the test articles after molding. The yield strain toughness was calculated by multiplying the shear stress by the square root of the shear strain. Three of the four test articles were annealed under an inert atmosphere for eight (8) hours at the temperatures indicated. The fourth test article was not annealed (raw).

FIG. 3 further demonstrates the improved yield strain toughness of molded articles made from a poly(p-dioxanone) polymer with an initial inherent viscosity (determined before melt processing) of greater than 2.1 dL/g. FIG. 4 shows similar yield strain toughness curves based on the inherent viscosity of poly(p-dioxanone) after it has been melt processed into test articles. Molded articles of poly(p-dioxanone) with inherent viscosity of about 2.1 dL/g, determined after molding, also have improved yield strain toughness values. Materials with high yield strain toughness are particularly desirable for melt processing into surgical articles such as surgical clips, pins, screws etc. Surgical articles made of materials with high yield strain toughness are able to bear higher loads without deforming. This, for instance, would allow a suture clip to generate a higher suture holding force.

Figure 5:
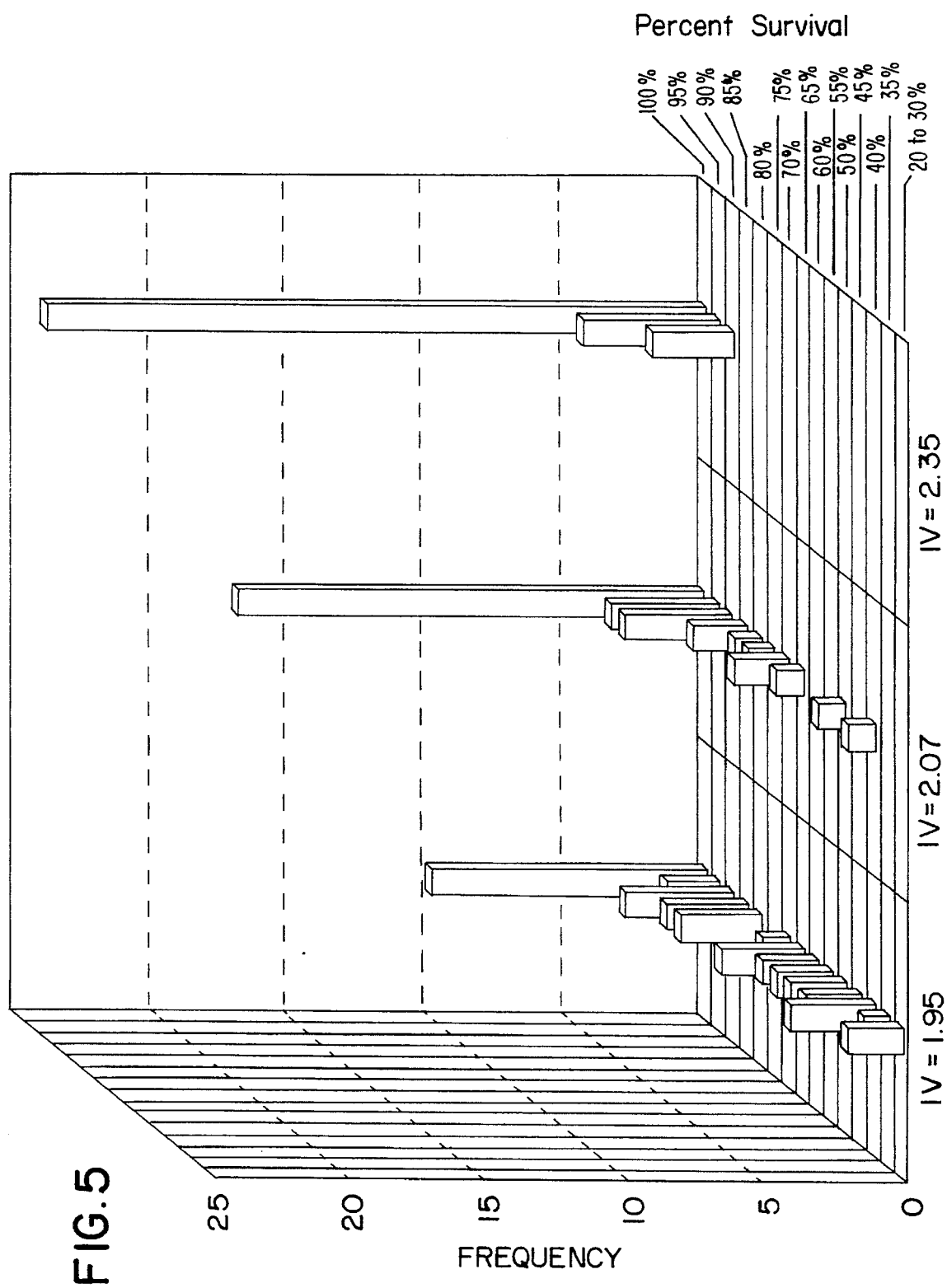
FIG. 5 graphically illustrates the improved in vivo survival of articles molded from high inherent viscosity poly(p-dioxanone) compared to test articles molded from poly(p-dioxanone) of a lower inherent viscosity.

FIG. 5 shows that surgical devices with hinges molded from poly(p-dioxanone), with an inherent viscosity above about 2.07 dL/g, have surprisingly improved in vivo survival rates compared to articles molded with an inherent viscosity of 1.91 dL/g. FIG. 5 demonstrates that as the inherent viscosity of the poly(p-dioxanone) used to manufacture suture clips was increased, the in vivo survival rate of the suture clips significantly improved. The in vivo survival of the suture clips were determined by locking a suture in the clip, implanting the suture clip in an animal and recovering the clip for evaluation fourteen days after implantation. If after the suture clip was recovered the latch was still closed and the hinge was not broken the clip was scored as intact. The percent survival was calculated by dividing the total number of clips that survived by the total number of clips evaluated and multiplying by 100 percent.

Similarly, significant improvements in surgical filament properties can also be achieved by increasing the inherent viscosity of the poly(p-dioxanone) polymer used to make filaments (from an inherent viscosity of about 1.72 dL/g to about 2.30 dL/g, determined at 25° C. at a concentration of 0.1 g/dL in hexafluoroisopropanol). As shown in Example IV the properties of a filament produced from a poly(p-dioxanone) polymer with a final inherent viscosity of about 2.3 dL/g, in an unoptimized extrusion and drawing process, showed a 31.5 percent improvement in straight tensile strength compared to fiber prepared from a polymer with an inherent viscosity of about 1.72 dL/g. The toughness of the filament, as defined by the tensile strength multiplied by the square root of the elongation to break, increased by 45 percent. The elongation and knot strength of the filament each also increased by about 20 percent.

To manufacture poly(p-dioxanone) with an inherent viscosity of 2.1 dL/g or above, the process employed must control the amount of chain growth initiators present in the polymerization reaction. This might have been previously accomplished by specifying that the monomer have a purity of greater than, for instance, 99.7% (excluding nonreactive diluents). However, it is extremely expensive to commercially produce monomer of greater than 99.7% purity. Additionally, because of the hydrophilic nature of this monomer, it is also difficult to avoid water contamination of the monomer after purification. Although starting with high purity p-dioxanone monomer is necessary to produce poly(p-dioxanone) having high inherent viscosity (HIV), other factors must be taken into consideration to reproducibly manufacture HIV poly(p-dioxanone).

The inherent viscosity of poly(p-dioxanone) is directly related to the molecular weight distribution of the polymer. The molecular weight of poly(p-dioxanone) is controlled in large measure by the number of polymer chains that are initiated during polymerization. Although the inventors do not wish to be limited by scientific theory, it is believed that for every mole of molecular weight control agent present, another mole of polymer chains is produced. Therefore, for a given batch size, the greater the number of chains that are initiated and thus formed, the lower the corresponding average molecular weight of the resultant polymer. Accordingly, to control the reaction to produce poly(p-dioxanone) of a precise molecular weight or inherent viscosity, the amount of molecular weight control agent that is needed must be precisely determined.

The amount of the molecular weight control agent employed is predetermined using a relationship which includes both the quantity and the purity of the p-dioxanone monomer. More specifically, a measure of the purity of the p-dioxanone monomer, "a monomer test of inherent viscosity", is performed in a separate p-dioxanone test polymerization. This monomer test of inherent viscosity reflects the free acid, water and miscellaneous impurities still normally contained in highly purified p-dioxanone monomer. Using the procedure outlined in Example I or a similar para-dioxanone monomer test, the inherent viscosities should be in the range of from about 2 dL/g to about 8 dL/g as determined at 25° C. at a concentration of 0.1 g/dL in hexafluoroisopropanol. Monomers with this level of purity can be used to produce high inherent viscosity poly(p-dioxanone) polymers. A preferred range of p-dioxanone test inherent viscosities for production of the high polymers of this invention are between 2.1 dL/g and 4.8 dL/g and are most preferred to be in the range of 3.0 to 4.4 dL/g. as determined at 25° C. at a concentration of 0.1 g/dL in hexafluoroisopropanol. Monomer lots that give low inherent viscosity values are unsuitable for producing high inherent viscosity polymer of the present invention. Monomer purification may be accomplished by methods well known to the practicing organic chemist. Recrystallization from a suitable solvent or by distillation are particularly useful methods.

Although the inventors do not wish to be limited by scientific theory, it is believed that the relationship between the overall monomer to all-molecular-weight-control-agents mole ratio ($R_o$) and the additives and impurities that can affect molecular weight is as follows:

$$1/R_o = 1/R_{mwca} + 1/R_w + 1/R_{fa} + 1/R_m \qquad (1)$$

where $R_o$=Overall monomer to all-molecular-weight-control-agents (including both intentionally added molecular control agents and impurities) mole ratio $R_{mwca}$=monomer to intentionally-added-molecular-weight-control-agent mole ratio $R_w$=monomer to water-contained-in-monomer mole ratio $R_{fa}$=monomer to free-acid-contained-in-monomer mole ratio $R_m$=monomer to reactive-miscellaneous-impurities mole ratio; refers to impurities generated via handling, etc.

A test polymerization for p-dioxanone monomer, in the absence of intentionally added molecular weight control agents, in practical terms, combines the effects of free acid, water, miscellaneous impurities, material handling, etc. into one measurable number that is correlatable to a particular monomer batch's ability to polymerize to high molecular weight.
Thus, $R_{iv}$=a mole ratio defined by the moles of monomer divided by the combined moles of free acid, water, miscellaneous reactive impurities, etc.
and, $$1/R_{iv}=1/R_w+1/R_{fa}+1/R_m \quad (2)$$

Combining equations 1 and 2 gives:

$$1/R_o=1/R_{mwca}+1/R_{iv} \quad (3)$$

We have discovered empirically that poly(p-dioxanone) prepared under a given set of conditions has a relationship of inherent viscosity (IV) to the overall ratio of moles of molecular weight control agent of the following form:

$$IV=A*R_o^a$$

where
a and A are constants in the equation $IV=A*R_o^a$ The values of the constants A and a will vary according to the polymerization conditions.
IV=inherent viscosity of poly(p-dioxanone) polymer and
$R_o$=overall ratio of moles of molecular weight control agent per mole of monomer.
Similarly, the inherent viscosity of the test polymerization is related to the moles of monomer per mole of combined impurities.

$$IV_m=K*R_{iv}^k \quad (4)$$

rearranging to solve for $R_{iv}$ $$R_{iv}=B*IV_m^b \quad (5)$$

where b and B are constants of the equation $R_{IV}=B*IV_m^b$ in which
$IV_m$=inherent viscosity of the poly(p-dioxanone) test polymerization
Substituting, the relationship between poly(p-dioxanone) polymer properties, molecular weight control agent and the inherent viscosity of a p-dioxanone monomer test polymerization into Equation (5) provides:

$$(A/IV)^{(1/a)}=1/R_{mwca}+1/(B*IV_m^b) \quad (6)$$

The constants a, A, b and B have been approximated to be as follows:
a=0.61–0.71
A=0.015–0.058
b=3.4–7.5
B=3.7–76
Using the test polymerization described in Example I the constants were determined to be a=0.66, A=0.03, b=4.8 and B=25.8. Inserting these values into Equation (6) and solving for $R_{mwca}$ provides:

$$1/R_{mwca}=0.005/IV^{1.51}-1/(25.8*IV_m^{4.8}) \quad (7)$$

In terms of grams of dodecanol per kilogram of p-dioxanone monomer (DDf):

$$DDf=9.19/IV^{1.51}-70.8/IV_m^{4.8} \quad (8)$$

The purity of the p-dioxanone monomer (as related to test inherent viscosity of the monomer) significantly affects the overall quantity of molecular weight control agent required to produce a high inherent viscosity polymer to within a relatively narrow IV range. Unless the purity level and impurities in the monomer are exactly the same for all monomer lots, without the correction for impurities one would not be able to reproducibly produce high inherent viscosity polymers. Thus, without correcting for monomer impurities, the inherent viscosity of poly(p-dioxanone) polymerized under the same conditions will vary widely.

The high molecular weight poly(p-dioxanone) polymer produced as described above can be processed to have a monomer content of not greater than 5 percent by weight and preferably not greater than 4 percent by weight, which is suitable for melt processing into a surgical device. One process which may be used to synthesize poly(p-dioxanone) comprises ring-opening polymerization of 2-oxo-1,4-dioxane or p-dioxanone in the presence of an initiator (such as dodecanol or other mono or di-functional alkanol), a catalyst (such as tin catalyst i.e., tin(II) caprylate or stannous octoate) at elevated temperature preferably in the range of from about 100° C. to about 150° C. in a dry inert atmosphere for about 2 to about 10 hours. It is currently preferred to perform the polymerization at a temperature in the range of from about 100° C. to about 120° C. because this temperature range provides an optimum balance between the reaction rate of the polymerization and the residual monomer content in the final polymer. The polymer produced by this process may then be further processed to increase conversion and/or to remove any unreacted monomer by vacuum drying the polymer or extruding the polymer through a vented twin screw extruder under conditions suitable to remove the unreacted monomer in the polymer. Those skilled in the art will readily be able to determine suitable extrusion conditions.

Alternatively, high inherent viscosity poly(p-dioxanone) polymer may be produced by charging a vessel with a catalyst (such as stannous octoate), an initiator (such as dodecanol or similar mono or di-functional alkanol) and heating the reaction vessel to a temperature in the range of from about 90° to about 140° C. for in the range of from about 30 minutes to about 5 hours. The polymer recovered from this reaction may then be allowed to complete its polymerization at a lower temperature in a conveniently sized container under an inert dry atmosphere at a temperature in the range of from about 60° to about 100° C. for in the range of from about 2 to about 7 days preferably from 3 to 5 days. Those skilled in the art will recognize that the reaction conditions can be optimized by varying time and temperatures. Longer reaction times allow reaction mass to more closely approximate the equilibrium monomer content for a given polymerizing temperature. The resultant polymers can be further processed to reduce residual monomer content by vacuum drying or similar processes. The polymers produced by this process also should be stored under a vacuum or inert atmosphere until they are used.

As previously stated, p-dioxanone can be copolymerized with up to 20 mole percent of another lactone monomer including but not limited to, glycolide, lactide, ε-caprolactone and trimethylene carbonate. The copolymerization can produce high inherent viscosity poly(p-dioxanone) by taking into account the monomer properties of the other lactone monomer as well as the p-dioxanone monomer properties as described above in Equation (1).

The polymers described above may be melt processed into surgical devices including but not limited to surgical devices selected from the group consisting of films, membranes, tapes, cords, pins(i.e. orthopaedic pins, produced by extrusion, oreintrusion or machining), clamps, screws, plates (i.e. maxillary prosthesis, temporary cranial plates and the like), clips (i.e. suture clips and ligating clips), staples, hooks, buttons, snaps, bone plugs, bone anchors, bone substitutes, cartilage substitutes, tubes, gauze, meshes, and filaments (i.e. monofilament, multifilament, bicomponent and heterologous braids, ligatures such as sutures, artificial tendons and ligaments). Particularly useful devices fashioned from the polymers described above include surgical clips which have a hinge component, such as those described in U.S. Pat. Nos. 4,620,541 and 5,160,339 assigned to Ethicon, Inc. and the receiver component from two piece fasteners as described in U.S. Pat. Nos. 4,805,617, 4,889,119 and 4,890,613 (all five patents are hereby incorporated by reference herein). Suitable methods of melt processing poly(p-dioxanone) polymers into these surgical devices is well known in the art. U.S. Pat. No. 4,052,988 (which is hereby incorporated by reference) describes one suitable method for melt extruding, orienting and annealing the fiber to form sutures. Similarly, U.S. Pat. No. 4,490,326 (which is hereby incorporated by reference) describes a molded device and a process for molding and annealing molded devices of poly(p-dioxanone).

Although in general, surgical filaments made from high inherent viscosity poly(p-dioxanone) may be manufactured using conventional manufacturing process for bioabsorbable monofilaments, it is currently preferred that the filament be manufactured according to the following guidelines.

The melt viscosity of the polymers of the present invention is important in determining the extrusion conditions which should be used. The melt viscosity of these polymers depends on the temperature and shear rate. Generally, these polymers may be extruded at a temperature in the range of from about 110° C. to about 190° C., preferably in the range of from about 135° C. to about 165° C. and most preferably in the range of from about 140° C. to about 165° C. Although melt viscosities can be reduced at higher temperatures, degradation occurs at higher temperature limiting in practical terms the temperatures that can be used. A single or multiple screw extruder can be used; additionally a melt pump can be employed to increase the precision of the melt throughput, thereby decreasing the variability of the fiber diameter.

The extrudate can be taken up after a controlled-temperature-air-quench or after being taken up though a liquid media quench bath. The extrudate may be extruded directly into the liquid bath or an air gap may be provided between the face of the extruder and the surface of the liquid bath. Currently, it is preferred to have an air gap of in the range of from about 0.25 to about 1.25 inches. The extrudate, for instance, can be taken up through a water quench bath. Currently it is preferred for the bath temperatures to be in the range of from about 20° C. to about 35° C. The rate of the extrusion as well as the quench temperature can have an effect on the properties of the extrudate, especially its morphology, and thus ultimately its drawability and the properties of the surgical filament so produced.

The extruded filaments can be allowed to partially crystallize. This can be accomplished by allowing the extrudate to stand at room temperature for a length of time prior to drawing, or by annealing the extrudate at elevated temperature, in a batch process or in-line process. The amount of time necessary to partially crystallize the extrudate is a function of the treatment temperature. At room temperature, several hours might be required to partially crystallize the extrudate; in general 24 hours has been found to be sufficient. At elevated temperatures, less time is needed to crystallize the extrudate. The crystallinity of the extrudate can also be increased in an in-line process prior to drawing by passing the fibers over heated godets or through an in-line annealing oven as is common in the practice of fiber production.

The extrudate is subsequently drawn in a one or multistage drawing process in order to achieve molecular orientation and improve tensile properties. The overall draw ratio can be as high as about 20X, but in general the overall draw ratios should be in the range of from about 4X to 7.5X and preferred are overall draw ratios between 4X and 5.5X.

Although the filament may be drawn using a number of methods, the following method is currently preferred. The extrudate is passed over several unheated godets and partially drawn. The partially drawn filament is then passed through an in-line oven and over an additional godet to complete the drawing process. The temperature of the oven can vary depending on the characteristics of the extrudate, the length of the oven, and the linear speed of the extrudate. Currently it is preferred that the oven be maintained at temperatures in the range of from about 190° C. to about 400° C. The godets can be used to heat the extrudate, as well as, an oven. The draw ratio in this first stage of drawing can vary. Generally, the first stage draw ratios will be in the range of from about 3X to about 20X, preferred are first stage draw ratios in the range of from 3X to 6X and most preferred is a first stage draw ratio of about 4X to about 5X.

The partially drawn fibers can then be drawn in a second stage draw operation. Draw temperatures in this second stage are generally higher than those employed for the first stage. The second stage draw may have a draw ratio of in the range of from about 0.75X to about 3X preferably the second draw ratio will be in the ratio of from about 1.01X to about 1.5X wherein the overall draw ratio of the first and second stage draw do not exceed 20X. As stated above it is currently preferred that the overall draw ratio of all the stages of the drawing process should be in the range of from about 4X to 7.5X. The resulting oriented filaments develop good straight and knot tensile strengths from a two-stage drawing process.

The speed of the godets in the drawing process will vary, but will generally be in the range of from about 10 feet per minute to about 200 feet per minute. For example if three godets are used in a two stage draw, the first godet should be in the range of from about 20 to about 30 feet per minute, the second godet should be in the range of from about 80 to about 120 feet per minute and the third godet should be in the range of from about 110 to about 145 feet per minute.

The resultant fiber can be taken up on a spool or can be relaxed slightly to give better handling characteristics. This is easily accomplished by allowing the fiber to pass over a set of godet rolls in which the linear speed of the second roll is slower than that of the first. This relaxation process is generally carried out at elevated temperature, either by heating the godet rolls or by allowing the fiber to pass through an in-line oven between the rolls.

Dimensional stability of the oriented filaments may be enhanced by subjecting the filaments to an annealing treatment. This treatment can consists of heating the drawn filaments to a temperature of from about 40° C. to about 100° C., most preferably from about 60° C. to 90° C. while restraining the filaments to control shrinkage. Annealing can conveniently be done in an in-line process or using a rack process. In a rack annealing process the filaments may be initially under tension or allowed to shrink up to about 20% prior to being restrained. The filaments are held at the annealing temperature for a few minutes to a few days or longer depending on the temperature and filament characteristics. In general, annealing for up to about 24 hours is satisfactory for the polymers of the invention. Optimum annealing time and temperature for maximum fiber in vivo strength retention and dimensional stability can be readily determined by simple experimentation for each fiber. Other spinning conditions than those shown here can also be employed without limiting the scope of this invention. Following annealing these filaments are commonly sterilized and singly or doubly armed with needles.

The poly(p-dioxanone) sutures produced from the polymer above should have an inherent viscosity of in the range of from 2.30 dL/g to about 3.5 dL/g and preferably in the range of from about 2.4 dL/g to about 3.5 dL/g. These sutures should have a straight tensile strength of from in the range of from about 80,000 psi to about 400,000 psi and preferably in the range of from 95,000 psi to about 400,000 psi. The knot strength of sutures made from these polymers should be at least about 45,000 psi and preferably in the range of from about 45,000 psi to about 100,000 psi.

The HIV poly(p-dioxanone) polymers of the present invention also can be molded or formed using many conventional molding techniques. Conventionally, poly(p-dioxanone) is injection molded by melting the polymer and injecting it at a volumetric flow rate of about 0.39 to about 0.47 cubic inches per second (which corresponds to an injection speed of about 1 to 1.2 inches per second when using an Engel Molding machine with a 0.71 inch (18 mm) diameter screw with a nozzle diameter of 0.125 inches) using the minimum hydraulic pressure necessary to fill the molds. Another method for injection molding poly(p-dioxanone) is described in U.S. Pat. No. 4,490,326, which issued Dec. 25, 1984 to Beroff et al. (which is hereby incorporated by reference). Beroff found that by maintaining the mold temperature under 35° C. that significant improvements in in vivo performance of ligating clips could be achieved. However, we have discovered that the injection molding HIV poly(p-dioxanone) can be substantially improved by increasing the volumetric flow rate of the polymer while maintaining the mold temperatures above 35° C. Currently, it is preferred that the mold temperatures used in injection molding HIV poly(p-dioxanone) be greater than 35° C., preferably in the range of from 36° C. to about 45° C. and most preferably in the range of from 36° C. to about 40° C. Additionally, it has been discovered that by increasing the volumetric flow rate from the conventionally used 0.47 cubic inches per second to at least 0.71 cubic inches per second (which corresponds to a injection rate of at least 1.8 inches per second when using an Engel Molding machine with a 0.71 inch (18 mm) diameter screw with a nozzle diameter of 0.125 inches) improves the properties of parts which are molded. Preferably the volumetric flow rate will be in the range of from about 0.71 cubic inches per second to about 2.37 cubic inches per second (which corresponds to an injection speed of from in the range of about 1.8 inches per second to about 6 inches per second when using an Engel Molding machine with a 0.71 inch (18 mm) diameter screw with a nozzle diameter of 0.125 inches) and most preferably the volumetric flow rate will be in the range of from about 0.79 cubic inches per second to about 1.58 cubic inches per second (which corresponds to an injection speed in the range of from about 2 inches per second to about 4 inches per second when using an Engel Molding machine with a 0.71 inch (18 mm) diameter screw with a nozzle diameter of 0.125 inches). Preferably the apparent wall shear rates at the nozzle of the injection molding machine will be in the range of from about 3,700 reciprocal seconds to 12,300 reciprocal seconds and most preferably in the range of from about 4,100 reciprocal seconds to about 8,200 reciprocal seconds.

Figure 6:
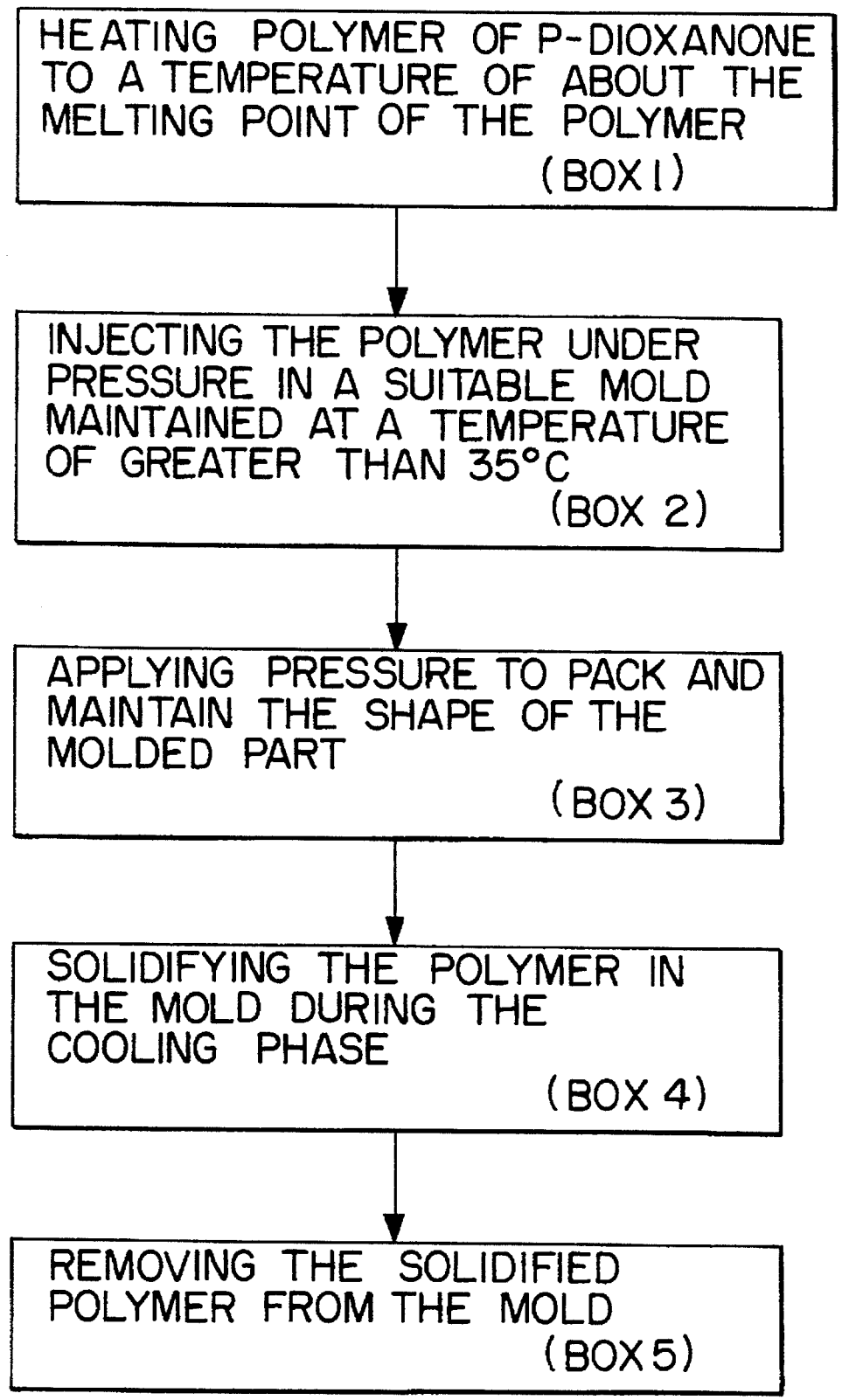
FIG. 6 is a schematic flow diagram showing the various steps in the method of molding high inherent viscosity poly(p-dioxanone).

Referring to the schematic flow sheet FIG. 6 the first step of the method is to heat the polymer to a temperature above the melting temperature of the polymer (Box 1). A suitable temperature range for melting poly(p-dioxanone) is in the range of from about 105° C. to about 140° C., preferably in the range of from about 110° C. to about 115° C. The specific apparatus used to melt poly(p-dioxanone) is not critical to the invention, as long as, it provides adequate temperature control. One suitable injection molding apparatus consists of a hydraulic ram and a reciprocating screw inside a heated barrel. The barrel temperature of this apparatus may be maintained at a temperature close to the melting temperature of the polymer allowing the combination of heat from the barrel and the shearing action of the screws to provide sufficient heat to melt the polymer to be injected through a suitable nozzle into a mold. Other techniques and apparatuses for melting polymers and maintaining polymers within a desired temperature range may also be used, including but not limited to, plunger-type molding apparatuses, injection molding apparatuses with separate accumulator devices and the like.

The molds used may be single cavity or multi-cavity molds. However, unlike the method of molding poly(p-dioxanone) described by Beroff et al., with HIV poly(p-dioxanone) it is preferred that the molds be maintained at a temperature above 35° C. and preferably in the range of from 36° C. to about 45° C. and most preferably in the range of from about 36° C. to about 40° C. (Box 2).

The polymer should be injected into the mold under pressure, preferably in the range of from about 500 to about 1650 pounds per square inch (Box 3). The injection pressure should be 30 psi above the minimum hydraulic pressure required to fill all the cavities in the mold and preferably will be in the range of from about 50 to about 75 psi above the minimum hydraulic pressure required to fill all the cavities in the mold. After the polymer is injected into the mold, pressure should be maintained on the polymer in the mold to pack and maintain its desired shape (Box 4). Currently, it is preferred that this hold pressure is in the range of from about 50 percent to about 85 percent of the initial pressure (in the range of from about 250 to about 1400 psi) maintained during the holding phase of molding cycle. Preferably the pressure maintained during the holding cycle will be in the range of from about 65 percent to about 85 percent of the initial pressure and most preferably about 75 percent of the initial pressure. The pressure should be maintained on the polymer for at least 3 seconds and preferably for at least 4 seconds. The molded device may be removed from the mold after a suitable cooling time (Box 5) of 75 to 120 seconds. Preferably the cooling time should be of a duration of 90 to 105 seconds. This molding process is particularly well suited to molding small surgical devices such as staples and clips where the mass of the molded device is less than 5 grams and preferably less than 2 grams.

Molded devices of poly(p-dioxanone) may be annealed and sterilized subsequent to molding. Annealing these molded devices is often done to stabilize or improve the properties of the device. Suitable techniques for annealing molded devices containing poly(p-dioxanone) are described in U.S. Pat. No. 4,620,541 issued on Nov. 4, 1986 to Gertzman et al. (which is hereby incorporated by reference). Sterilization may be accomplished by any suitable means known to those skilled in the art.

The following non-limiting Examples are provided to further illustrate the present invention.

EXAMPLE I

This example describes a method for testing p-dioxanone monomer for its suitability for making high molecular weight poly(p-dioxanone).

To a clean, dry glass ampoule having a neck approximately 30 cm in length, 14 mm in internal diameter, terminating first in a swollen neck section to accommodate solids overflow during loading and finally in a spherical bulb of approximately 25 mL of internal volume, is charged a clean, dry magnetic spin bar, 20.0 grams of p-dioxanone monomer to be tested, and 0.039 mL of a 0.0331M stannous octoate in toluene solution. The transfer is generally conducted in a dry nitrogen glove box so as not to expose the ingredients to atmospheric moisture and care is taken not to leave deposits on the neck of the ampoule.

The ampoule is connected to a vacuum manifold and purged with dry nitrogen to remove the small amount of toluene present. The ampoule is evacuated to a pressure of 100 microns for a period of 40 to 45 minutes. After this time, the pressure is adjusted with dry nitrogen to correspond to 5 inches of Hg, and the ampoule is hermetically sealed by collapsing shut the upper region of the neck by flaming with a suitable torch. The charged ampoule is immersed in a silicon oil bath preheated to 120° C., and positioned above a suitable magnetic stirrer. Mixing by virtue of the spin bar/stirrer system is begun almost immediately; as polymer is formed the molten mass becomes too viscous for the magnetic spin bar to be effective and the stirrer is shut off. After 20 hours of heating at 120° C., the ampoule is carefully removed from the oil bath, wiped with a clean cloth to remove silicon oil from the surface, and set aside to cool to room temperature.

The reaction mass, a combination of formed polymer and residual unreacted monomer, is isolated by immersing the ampoule in liquid nitrogen followed by breaking the glass away, typically with a hammer. The reaction mass is sampled by using a twist drill and bit, drilling at a slow rate of approximately 1 revolution per second into the center of the mass approximately ½ inch down. The inherent viscosity of pieces removed from the center section of the "test egg" is determined in hexafluoroisopropanol.

EXAMPLE II

This example describes a process for producing poly(p-dioxanone) with a high inherent viscosity.

Poly(p-dioxanone) polymer can be produced either in a one-step polymerization in a reactor capable of handling high viscosity polymers or in a two-step polymerization whereby a low molecular weight pre-polymer is transferred to curing trays for a second stage solid state polymerization to achieve maximum conversion.

Formula

The example described herein is formulated for the two step prepolymer/solid state polymerization. For this example 182.2 moles (18.584 kg) of p-dioxanone monomer of average test inherent viscosity 3.31 dL/g were used to produce a high IV poly(p-dioxanone) polymer of target inherent viscosity of 2.61 dL/g and a melt index of 0.035 g/10 min. as determine with standard ASTM equipment at 150° C. with an added weight of 6,600 g using a modified ASTM cylindrical die with a 0.0260 inch diameter. The quantity of molecular weight control agent added to the polymerization is the difference between the estimated number of moles of MWCA based on overall moles of monomer per mole of MWCA and the number of moles of MWCA contained in the monomer as impurities. Based on Equation (3) above, an overall ratio of 849 moles of monomer per mole of combined molecular weight control agents was required to provide a polymer of desired properties. The combined impurities of the p-dioxanone monomer with a test polymerization of 3.31 dL/g was estimated to account for 0.0001208 moles of MWCA as impurities (8279 moles of impurity type molecular weight control agent per mole of monomer). The amount of actual molecular weight control agent added to the reaction was determined per Equation 2, to be 0.0010571 moles of molecular weight control agent per mole of monomer (or 946 moles of monomer per mole of molecular weight control agent). Stannous octoate catalyst in the range of from about 10,000 to about 100,000 moles of monomer per mole of catalyst can be used for solid state polymerization. The example described herein used a 0.331 molar stannous octoate catalyst solution at a ratio of 25,000 moles of monomer per mole of stannous octoate. The optimum catalyst level is a function of dye level and type, as well as, polymerization temperature. At too low a catalyst ratio the polymerization is extremely slow and will not result in the complete conversion of monomer to polymer. At too high a catalyst ratio the polymer will degrade when reheated during melt processing.

Procedure

Approximately half of the 182.2 moles of p-dioxanone monomer (test IV=3.31 dL/g) was charged to a preheated (65° C.) fifteen gallon stainless steel reactor while being purged with nitrogen. The polymerization can take place with or without reactor preheating. D&C violet #2 dye (18.6 g or 0.1 wt % of the charged monomer) was mixed with a portion of the monomer and added to the reactor. The remaining portion of p-dioxanone monomer was then added to the reactor. The amount of dodecanol to be added was calculated using Equation (8). The calculated quantity of dodecanol (35.9 g), the intentionally added molecular weight control agent, was added to the reactor also while under a nitrogen purge. Stannous octoate catalyst (22.04 mL of a 0.331 molar solution in toluene) was then added to the reactor, again under a nitrogen purge to prevent the addition of moisture. The reactor was sealed. The pressure in the reactor was reduced to 1000 microns or less, maintained there for twenty minutes and then nitrogen introduced to develop an overpressure of 0–2 psig. This evacuation/ nitrogen purge step was repeated a total of three times. The oil circulating through the jacket was increased to 110° C. to initiate polymerization. When the batch temperature reached 90° C. (in about 15 minutes), the oil temperature was reduced to 95° C. Polymer viscosity, as determined with a Brookfield Model DV-II Viscometer using a no. 2 spindle, was monitored by removing a portion of the molten mass through a valve located at the bottom of the reactor. The entire contents of the reactor were discharged under nitrogen into curing trays when a viscosity between 100 and 500 cp had been reached. A curing tray consists of a sealable container made of metal, plastic or other suitable material which does not deform or degrade at 120° C. and does not react with the polymerization mass to render it unsuitable. The trays used herein are 9 inch diameter formed-aluminum trays. A teflon or teflon coated metal lid is used to provide the closed storage container during curing.

The curing trays were sealed under nitrogen blanket and placed into a nitrogen-purged oven set at 80° C. We have found that reaction temperatures between about 65° and 95° C. are suitable for a solid-state post curing, but that temperatures between 70° and 90° C. are preferred, and most preferred is about 80° C. The reaction mass can be heated for between about two and seven days depending on the curing temperature. We have found that at 80° C., a curing time between three and five days is suitable. The polymer of this example was cured at 80° C. for 4 days.

The cured polymer was removed from the oven, allowed to cool to room temperature and then removed from the curing trays. The polymer was sampled to determine properties, weighed, placed in plastic bags and then transferred to freezer storage until required for the next step, size reduction. The cold and brittle polymer was removed from freezer storage and immediately placed in a Cumberland grinder for size reduction. A 3/16 inch grinder screen was used to provide the desired particle size. The ground polymer was then sieved in conventional size separation equipment to remove fines (less than 18 mesh) and over-sized pieces of polymer (greater than ¼ inch). The ground and sieved polymer was then transferred to a vacuum tumble dryer to reduce the small amount of unreacted monomer. The drying cycle consisted of a 10 hour vacuum phase without heat to remove moisture picked during size reduction, a 32 hours heat and vacuum phase to remove unreacted monomer, followed by a cool-down phase to allow the polymer to approach room temperature while still under vacuum. The dryer achieved a vacuum corresponding to a pressure of 200 microns or less at the end of the devolatilization cycle. The dried polymer was then transferred to vacuum storage vessels and placed under vacuum to await disposition. Test samples were removed during dryer discharge.

The resultant polymer had an inherent viscosity of 2.53 and a melt index of 0.043 g/10 min. The melting point, as determined by DSC (first heat) using a scan rate of 20° C./min, was determined to be 119° C.

EXAMPLE III

Suture knot clips were molded from several different inherent viscosities of poly(p-dioxanone) produced following the process described in Example II. The data from in vivo testing of these knot clips demonstrates that a significant improvement in knot clip in vivo survival can be achieved by increasing the molecular weight of poly(p-dioxanone).

Three grades of poly(p-dioxanone) with inherent viscosities respectively of from 1.91 dL/g, 2.07 dL/g and 2.35 dL/g (all determined at 25° C. at a concentration of 0.1 g/dL in hexafluoroisopropanol) were evaluated in molded suture knot clips possessing both a hinge and a latch design similar to the suture knot clip design described in EPA-519,703 (hereby incorporated by reference). The three grades of poly(p-dioxanone) were melted at a temperature of from 104°–112° C. The melted polymer was injected molded using a 30 ton Engel OM361-002 molding machine with a 0.71 inch diameter (18 mm) screw and a nozzle diameter of 0.125 inches fitted with a four cavity mold. The melted polymer was injected with a boost pressure of from 625–1125 psi. The molds were maintained at a temperature of 39°–53° C. The molded parts were ejected after 75 to 105 seconds.

The suture knot clips were then locked on a 2/0 coated Vicryl™ suture and implanted in rats. Fourteen days later the knot clips were carefully removed from the rats and evaluated. The clips were evaluated to determine if the latches remained closed and the hinges remained intact. A clip was considered to have survived in vivo if the latch was still completely closed over the suture strand and the hinge was not broken when the clips were removed from the rats. The data from these tests are presented graphically in FIG. 5.

The data in FIG. 5 conclusively demonstrates that with an inherent viscosity of 1.91 dL/g only 16 of 40 sample groups tested have a 90% survival rate for suture knot clips. Increasing the inherent viscosity to 2.07 dL/g results in 25 of 36 sample groups tested having a 90% survival rate for the suture knot clips. However, increasing the inherent viscosity to 2.35 dL/g results in all 32 sample groups tested having a 90% survival rate and 24 out of 32 groups having a 100% survival rate.

Thus, by increasing the inherent viscosity of poly(p-dioxanone) (from 1.91 dL/g to 2.07 dL/g) used in molding suture clips, the in vivo survival of the clips can be significantly increased.

EXAMPLE IV

This example provides a comparison of the properties of poly(p-dioxanone) sutures having an initial inherent viscosity of 1.71 dL/g and 2.28 dL/g. This sutures were prepared under the following conditions:

TABLE I

| POLY(p-DIOXANONE) SUTURES | | |
|---|---|---|
| Initial IV of Polymer | 1.72 dL/g | 2.64 dL/g |
| IV of Polymer after Extrusion | <1.72 dL/g | 2.28 dL/g |
| Temperatures °C. | | |
| Barrel Zones 1/2/Flange | 114/117/119 | 145/155/148 |
| Pump | 119 | 155 |
| Block | 119 | 158 |
| Die | 122 | 154 |
| Quench Conditions | | |
| Air Gap, Inch | ½ | ¼ |
| Water Temp, °C. | 22 | 25 |
| Roll Speed, FPM | 9.5 | 23 |
| Air Quench Cabinet Temp °C. | 115 | AMB |
| Drawing Conditions | | |
| Speed, FPM | 9.5 | 24 |
| Godet 1 Speed, FPM | 10 | 25 |
| Godet 2 Speed, FPM | 52 | 109 |
| Oven Temp, °C. | 220 | 325 |
| Godet 3 Speed, FPM | 60 | 130 |
| Draw Ratios | | |
| First Stage | 5.2 | 4.4 |
| Second Stage | 1.15 | 1.19 |
| Total Draw Ratio | 6.0 | 5.2 |

The characteristic properties of the sutures of the invention are readily determined by conventional test procedures. The tensile properties (i.e., straight and knot tensile strengths and elongation) displayed herein were determined with an INSTRON tensile tester. The settings used to determine the straight tensile, knot tensile and break elongation were the following:

TABLE II

| | GAUGE LENGTH (cm) | CHART SPEED (cm) | CROSSHEAD SPEED (cm/min) |
|---|---|---|---|
| STRAIGHT TENSILE | 12.7 | 30.5 | 30.5 |
| KNOT TENSILE | 12.7 | 30.5 | 30.5 |
| BREAK ELONGATION | 12.7 | 30.5 | 30.5 |

The straight tensile strength is calculated by dividing the force to break by the initial cross-sectional area of the suture. The elongation at break is read directly from the stress-strain curve of the sample.

The knot tensile strength of a suture is determined in separate tests. The surgeon's knot is a square knot in which the free end is first passed twice, instead of once, though the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber. The tensile strength values are reported as KPSI (which means PSI X $10^3$).

TABLE III

| PHYSICAL PROPERTIES OF Poly(p-dioxanone) Sutures | Poly(p-dioxanone) IV 1.72 Initial Polymer Viscosity | Poly(p-dioxanone) IV 2.64 Initial Polymer Viscosity |
|---|---|---|
| Diameter, MIL | 16.8 | 15.8 |
| Strengths, KPSI | | |
| Straight, KPSI | 73.9 | 97.2 |
| Knot, KPSI | 40.2 | 48.5 |
| Elongation, % | 26.3 | 32.2 |
| Toughness, $TE^{1/2}$ KPSI | 379 | 551 |

The data in Table II demonstrates the very significant changes in straight strength, knot strength and elongation which occur where the molecular weight of poly(p-dioxanone) is increased in sutures. The straight strength of the suture increased by 31.5 percent and the knot strength and elongation of the suture increased by greater than 20 percent. The toughness of the fiber also increased by greater than 45 percent (tensile strength multiplied by the square root of elongation to break).

It should be recognized that the extraordinary improvement in the properties of the high inherent viscosity filament were obtained using an unoptimized extrusion and drawing process. Therefore, it is expected that by routine experimentation the temperature for extrusion and the draw ratios for orienting the filament can be optimized to further improve the properties of filaments made from high inherent viscosity poly (p-dioxanone).

EXAMPLE V

This Example describes the mechanical testing procedures for injection molded poly(p-dioxanone) tensile bar test articles. The data from the mechanical tests is presented in FIG. 1–4.

Three lots of poly(p-dioxanone) polymer, having different inherent viscosities, were molded into tensile bar test articles (dogbones) for mechanical testing. A poly(p-dioxanone) resin exhibiting an inherent viscosity of 1.86 dL/g was molded into tensile bar test articles using an Arburg Model 170-CMD/E injection molder with a size 15 mm plasticizing cylinder and equipped with a general purpose screw; the hopper was outfitted with a nitrogen purge to keep the resin dry. The feed, transition, and compression zone temperatures were 121°, 143°, and 143° C., respectively, while the nozzle and mold temperatures were 129° and 40° C. A maximum injection speed of 12 cc/sec was used. The injection pressure experienced was 2495 bars. For each cycle, a total hold-time-under-pressure of 11 seconds was used and the mold was held closed for 40 seconds; a typical cycle time was 58 seconds.

Two poly(p-dioxanone) resins exhibiting inherent viscosities of 2.13 and 2.43 dL/g respectively were molded into tensile bar test articles (dogbones) using an Arburg Model 170-90-200 injection molder with a size 18 mm plasticizing cylinder and equipped with a general purpose screw; the hopper was outfitted with a nitrogen purge to keep the resin dry. Molding conditions including specific machine settings are shown in Table IV below:

TABLE IV

| Inherent Viscosity of the Resin, dL/g: | | 2.13 | 2.43 |
|---|---|---|---|
| Feed Zone Temperature, °C.: | | 108 | 114 |
| Transition Zone Temperature, °C.: | | 109 | 116 |
| Compression Zone Temperature, °C.: | | 109 | 116 |
| Nozzle Temperature, °C.: | | 110 | 117 |
| Melt Temperature,, °C.: | | 107–108 | 114–115 |
| Mold Temperature, °C.: | | 39–40 | 39–40 |
| Hydraulic Pressure, psi | | | |
| | Boost: | 1600 | 2000 |
| | Hold: | 1200 | 1250 |
| Mold Closing: | V1 | 3 | 3 |
| | P1 | 10 | 10 |
| | V2 | 1 | 1 |
| Injection Speeds: | V3 | 90 | 95 |
| | V4 | 90 | 95 |
| Injection Pressures: | P2 | 70 | 90 |
| | P3 | 50 | 55 |
| | P4 | 00 | 00 |
| Screw Speed: | V5 | 45 | 45 |
| Screw RPM: | | 200 | 200 |
| Back Pressure: | P5 | 25 | 25 |
| Mold open: | V6 | 3 | 3 |
| | V7 | 2 | 2 |
| Knock Out Forward: | V10 | 2 | 2 |
| | P8 | 2 | 2 |
| Knock Out Return: | V11 | 1 | 1 |
| | P9 | 1 | 1 |
| Cycle Time, sec: | t1 | 72.6 | 73.5 |
| Injection Time, sec: | t2 | 3.0 | 3.0 |
| | t3 | 5.0 | 5.0 |
| | t4 | 3.0 | 3.0 |
| Cooling Time, sec: | t5 | 50.0 | 50.0 |
| Die Open Time, sec: | t6 | 0.5 | 0.5 |
| Mold Protect Time, sec | t7 | 2.0 | 2.0 |
| Delayed Injection Time, sec: | t8 | 2.0 | 2.0 |

In general, high molecular weight poly(p-dioxanone) polymers generate higher melt viscosities than corresponding moderate molecular weight polymers, leading to higher processing pressures. It is common to offset high melt viscosities by employing processing temperatures but this has a practical limit due to the increased degradation that occurs at higher temperatures. Some injection molding machines are incapable of generating the pressures required to mold higher molecular poly(p-dioxanone) resins. Thus, to fully benefit from the increased properties that the polymers of the subject invention can provide, machines capable of generating the pressures required to process said resins must be employed.

The mechanical properties of injection molded dogbone test articles were determined using a Model 4201 Instron Tensile Testing machine equipped with an Instron 10 mm gauge length, self-identifying, strain gauge extensometer having a maximum strain specification of 50 percent. The machine was operated with a crosshead speed of 0.50 inches per minute. The molded dogbone test articles were 3.26 inches in overall length and 0.040 inches thick. The two tab sections of the dogbones were each 0.375 inches wide by 1.00 inches long; the uniform central gauge section was 0.600 long by 0.125 inches wide (and 0.040 inches thick). The transition section connecting the two tab sections to the central gauge section was defined by a radii of 0.500 inches tangent to the gauge section.

EXAMPLE VI

The data in Example III conclusively demonstrates that significantly improved in vivo survival of suture knot clips can be obtained by increasing the molecular weight of poly(p-dioxanone). In this example, it will be demonstrated that certain changes in the injection molding of suture clips lead to further significant improvements in the in vivo survival and tensile properties.

Poly(dioxanone) polymers with inherent viscosity respectively of from 1.87 to 1.92 dL/g (determined at 25° C. at a concentration of 0.1 g/dL in hexafluoroisopropanol) were used to make suture knot clips possessing both a hinge and a latch. The polymers were melted with melt temperatures between 104° to 107° C. and the melted polymers were then injection molded using the conditions listed in Processing Condition I in Table V using a 30 ton Engel molding machine with a 0.71 inch diameter (18 mm) screw and a nozzle diameter of 0.125 inches fitted with a 4 cavity mold. The injection pressure was the minimum hydraulic pressure required to fill the mold. The injection speed of 1.0 to 1.2 inches per second corresponds to a volumetric flow rate of 0.39 to 0.47 cubic inches per second with an apparent wall shear rate of 2100 to 2500 reciprocal seconds at the nozzle.

TABLE V

| Process Parameter | Processing Condition I | Processing Condition II | Processing Condition III |
| --- | --- | --- | --- |
| Mold Temperature (°C.) | 39–45 | 38–44 | 36–40 |
| Hold Time (sec) | 4 | 4 | 4 |
| Cooling Time (sec) | 60–70 | 100 | 100 |
| Injection Pressure (psi) | Minimum Hydraulic Pressure required to fill the mold | Minimum Hydraulic Pressure to fill the mold + 50 psi | Minimum Hydraulic Pressure to fill the mold + 50 psi |
| Hold pressure | 450–550 psi | 75% of Injection Pressure | 75% of Injection Pressure |
| Injection Speed (in/sec) | 1.0–1.2 | 1.2 | 2.4 |

The suture knot clips were then locked or clamped on a 3/0 coated Vicryl™ suture and implanted in rats. Ten days later the knot clips were carefully removed from the rats and evaluated. The clips were evaluated to determine if the latches remained closed and the hinges remained intact. A clip was considered to have survived in vivo, if the latch was completely closed over the suture strand and the hinge was not broken when the clips were removed from the rats. Ten random clips were tested for 10 days. For clips made from polymers with inherent viscosity respectively of from 1.87 to 1.92 dL/g, all clips successfully survived for 10 days.

A poly(dioxanone) polymer with inherent viscosity of 2.18 dL/g (determined at 25° C. at a concentration of 0.1 g/dL in hexafluoroisopropanol) was used to make suture knot clips possessing both a hinge and a latch using injection molding technique. The molding machine used was a 30 ton Engel molding machine with a 0.71 inch diameter (18 mm) screw and a nozzle diameter of 0.125 inches fitted with a 8 cavity mold with 4 inner and 4 outer cavities. The conditions used to mold the knot clips are described as Process Condition II in Table V. Although the inherent viscosity of polymer was higher than the inherent viscosity of the polymer used to make clips following Process Conditions 1, the injection molding conditions were similar. The polymer was melted using barrel set point settings of 106° C. in the feed zone and temperatures settings in the other 3 zones of the barrel and in the nozzle were the same for any particular run and varied between 106° to 108° C. The mold temperature varied from 38° to 44° C. The injection pressure was 50 psi above the minimum hydraulic pressure required to fill the mold. The injection speed of 1.2 inches per second corresponds to a volumetric flow rate of 0.47 cubic inches per second with an apparent wall shear rate of 2500 reciprocal seconds at the nozzle. The other molding conditions used are listed in Processing Condition II in Table V.

The suture knot clips were then locked or clamped on a 2/0 coated Vicryl™ suture and implanted in rats. The 2/0 coated Vicryl™ has a larger diameter than the 3/0 suture which the knot clips from Process Condition I were previously tested on. Fourteen and sixteen days later, the knot clips were carefully removed from the rats and evaluated. The clips were evaluated to determine if the latches remained closed and the hinges remained intact. A clip was considered to have survived in vivo if the latch was completely closed over the suture strand and the hinge was not broken when the clips were removed from the rats. Also, the clips were visually inspected to determine the relative level of cracking that occurred in the explanted clips. Forty random clips (5 per cavity) were tested for fourteen and sixteen days in vivo survival.

The data in Table VI shows the tensile properties of inner and outer cavities and the in vivo survival after sixteen days. Inner and Outer in Table VI refers to an average value of tensile properties obtained from four inner and four outer cavities, respectively; ten clips were tested per cavity. Hinge refers to maximum tensile load (in pounds) demonstrated by the suture knot clip during tensile testing using Instron Tensile Testing Machine with attachments to grip the two beams of the suture knot clip. Elong. refers to the elongation values (in inches) at break in the hinge area of the suture knot clip during tensile testing. Energy refers to energy at break (in pound-inch) during tensile testing and is measured as the area under load-displacement curve obtained during tensile testing. It is evident that suture knot clips from outer cavities have lower properties than suture knot clips from inner cavities. At fourteen days three groups of suture knot clips had a 100 percent survival and one group had less than 100 percent survival. At sixteen days two groups had 100 percent survival and two groups had less than 100 percent survival. All the in vivo failures were observed with clips molded in the outer cavities. The level of cracking in general was more pronounced at sixteen days as compared to fourteen days. The crack evaluations demonstrated that the clips from the outer cavities have more cracking compared to clips from inner cavities from the same processing conditions. Although there were still some fourteen and sixteen day in vivo failures on knot clips from Process Condition II, it is still evident that the use of higher inherent viscosity poly(p-dioxanone) in Process Condition II allows the clips to survive for longer in vivo periods under the greater strain of a larger diameter suture as compared to the lower inherent viscosity polymer used in Process Condition I.

rats and evaluated. The clips were evaluated to determine if the latches remained closed and the hinges remained intact. A clip was considered to have survived in vivo if the latch was completely closed over the suture strand and the hinge was not broken when the clips were removed from the rats. Also the clips were visually inspected to determine the relative level of cracking that occurred in the explanted clips. Forty random clips (5 per cavity) were tested for 16 days in vivo survival.

The data in Table VII shows the tensile properties of inner and outer cavities and the in vivo survival after 16 days. It is clearly evident that suture knot clips from outer cavities have lower elongation at break and lower energy to break than suture knot clips from inner cavities and the hinge

TABLE VI

| Melt Temp/<br>Mold Temp/<br>Injection<br>Pressure | Inner<br>Hinge<br>(lb) | Outer<br>Hinge<br>(lb) | Inner<br>Elong.<br>(in) | Outer<br>Elong.<br>(in) | Inner<br>Energy<br>(lb-in) | Outer<br>Energy<br>(lb-in) | 16 Day<br>In<br>Vivo<br>Survival |
|---|---|---|---|---|---|---|---|
| 106° C./44° C.<br>1096 psi | 11.6 | 10.3 | 0.069 | 0.051 | 0.612 | 0.397 | 95% |
| 106° C./38° C.<br>1149 psi | 12.3 | 9.7 | 0.084 | 0.056 | 0.750 | 0.409 | 100% |
| 108° C./42° C.<br>1051 psi | 11.2 | 9.8 | 0.073 | 0.056 | 0.598 | 0.419 | 100% |
| 108° C./38° C.<br>1072 psi | 12.3 | 10.0 | 0.084 | 0.058 | 0.761 | 0.424 | 95% |

Poly(p-dioxanone) polymer with inherent viscosity of 2.18 dL/g (determined at 25° C. at a concentration of 0.1 g/dL in hexafluoroisopropanol) was used to make suture knot clips possessing both a hinge and a latch using injection molding technique and using a 30 ton Engel molding machine with a 0.71 inch diameter (18 mm) screw and a nozzle diameter of 0.125 fitted with a 8 cavity mold with 4 inner and 4 outer cavities. The polymer was melted using barrel set point settings of 106° C. in the feed zone and temperatures settings in the other 3 zones of the barrel and in the nozzle are same for any particular run and was varied between 110° to 114° C. The mold temperature varied from 36° to 40° C. The injection speed of 2.4 inches per second corresponds to a volumetric flow rate of 0.94 cubic inches per second and an apparent wall shear rate of 4900 reciprocal seconds at the nozzle. The injection pressure was 50 psi above the minimum hydraulic pressure required to fill the mold. The other conditions are specified in Processing Condition III in Table V.

The suture knot clips were then locked or clamped on a 2/0 coated Vicryl™ suture and implanted in rats. Sixteen days later the knot clips were carefully removed from the strengths are almost identical between inner and outer cavities. However, the tensile properties in Table VII were significantly higher than shown in Table VI. There were no in vivo failures in clips from either inner or outer cavities. The crack evaluations revealed that there was no significant difference in cracking between clips from outer and inner cavities from the same processing conditions arising out of higher injection speeds and lower mold temperatures. The in vivo results in Table VII showed significant improvements compared to the results reported in Table VI.

TABLE VII

| Melt Temp/<br>Mold Temp/<br>Injection<br>Pressure | Inner<br>Hinge<br>(lb) | Outer<br>Hinge<br>(lb) | Inner<br>Elong.<br>(in) | Outer<br>Elong.<br>(in) | Inner<br>Energy<br>(in-lb) | Outer<br>Energy<br>(in-lb) | 16 Day<br>In<br>Vivo<br>Survival |
|---|---|---|---|---|---|---|---|
| 110° C./40° C./1106 psi | 12.3 | 12.1 | 0.095 | 0.086 | 0.886 | 0.786 | 100% |
| 114° C./40° C./975 psi | 12.1 | 12.0 | 0.091 | 0.085 | 0.822 | 0.770 | 100% |
| 114° C./36° C./995 psi | 12.6 | 12.5 | 0.099 | 0.091 | 0.947 | 0.865 | 100% |
| 110° C./36° C./1051 psi | 12.8 | 12.5 | 0.106 | 0.089 | 1.018 | 0.840 | 100% |

It should be recognized that the significant improvement in the properties and in vivo performance of the high inherent viscosity suture knot clips was obtained using higher volumetric injection rates and lower mold temperature.

We claim:

1. A process for producing molded surgical devices from high inherent viscosity poly(p-dioxanone) comprising a) heating poly(p-dioxanone) with an inherent viscosity in the range of from about 2.10 dL/g to about 3.5 dL/g to a temperature in the range of from about 105° C. to about 140° C. to form a melted poly(p-dioxanone); then b) injecting said melted poly(p-dioxanone) into a mold at a volumetric flow rate of greater than 0.70 cubic inches per second wherein said mold is being maintained at a temperature above 35° C.;

c) cooling said melted poly(p-dioxanone) sufficiently to maintain its shape while in the mold and thereby forming a hardened poly(p-dioxanone) device; and d) removing said hardened poly(p-dioxanone) from the mold.

2. The process of claim 1 wherein the melted poly(p-dioxanone) is injected into the mold at a volumetric flow rate of in the range of from about 0.71 cubic inches per second to about 2.37 cubic inches per second.

3. The process of claim 1 wherein the pressure is maintained on the melted poly(p-dioxanone) in the mold as the melted poly(p-dioxanone) is cooling to pack the melted poly(p-dioxanone) to maintain the desired shape.

4. The process of claim 1 wherein the mold temperature is in the range of 36° C. to about 45° C.

5. The process of claim 1 wherein the poly(p-dioxanone) is heated to a temperature in the range of from about 110° C. to about 140° C.

6. The process of claim 3 wherein the melted poly(p-dioxanone) is injected into the mold at a pressure in the range of from about 500 psi to about 1,650 psi.

7. The process of claim 1 wherein the melted poly(p-dioxanone) is injected into the mold through a nozzle with an apparent wall shear rate at the nozzle of in the range of from about 3,700 reciprocal seconds to about 12,300 reciprocal seconds.

8. The process of claim 7 wherein at least 50 percent of the injection pressure is maintained on the melted poly (p-dioxanone) while the melted poly (p-dioxanone is packing.

9. A process for producing molded surgical devices from high inherent viscosity poly(p-dioxanone) comprising a) heating poly(p-dioxanone) with an inherent viscosity in the range of from about 2.10 dL/g to about 3.5 dL/g to a temperature in the range of from about 105° C. to about 140° C. to formed a melted poly(p-dioxanone); then b) injecting said melted poly(p-dioxanone) at a volumetric flow rate of in the range of from about 0.71 cubic inches per second to about 2.37 cubic inches per second into a mold wherein said mold is being maintained at a temperature above 35° C.;

c) packing said melted poly(p-dioxanone) sufficiently to maintain its shape while in the mold under pressure in the range of from about 200 psi to about 1400 psi and subsequently cooling the melted poly(p-dioxanoe) thereby forming a hardened poly(p-dioxanone) device; and d) removing said hardened poly(p-dioxanone) device from the mold.

* * * * *